US012400750B1

(12) United States Patent
Jin et al.

(10) Patent No.: US 12,400,750 B1
(45) Date of Patent: Aug. 26, 2025

(54) AUTOMATIC CONTENT TAGGING IN VIDEOS OF MINIMALLY INVASIVE SURGERIES

(71) Applicant: Verily Life Sciences LLC, South San Francisco, CA (US)

(72) Inventors: Xing Jin, San Jose, CA (US); Joëlle Barral, Mountain View, CA (US)

(73) Assignee: Verily Life Sciences LLC, Dallas, TX (US)

( * ) Notice: Subject to any disclaimer, the term of this patent is extended or adjusted under 35 U.S.C. 154(b) by 969 days.

(21) Appl. No.: 16/949,785

(22) Filed: Nov. 13, 2020

Related U.S. Application Data

(60) Provisional application No. 62/935,899, filed on Nov. 15, 2019.

(51) Int. Cl.
| | | |
|---|---|---|
| *G16H 20/40* | (2018.01) |
| *G06N 5/02* | (2023.01) |
| *G16H 30/40* | (2018.01) |
| *G16H 40/63* | (2018.01) |

(52) U.S. Cl.
CPC ............ *G16H 20/40* (2018.01); *G06N 5/02* (2013.01); *G16H 30/40* (2018.01); *G16H 40/63* (2018.01)

(58) Field of Classification Search
CPC ........ G16H 20/40; G16H 30/40; G16H 40/63; G06N 5/02
See application file for complete search history.

(56) References Cited

U.S. PATENT DOCUMENTS

| | | | | |
|---|---|---|---|---|
| 2016/0048964 | A1* | 2/2016 | Kruglick | G06V 10/50 |
| | | | | 382/103 |
| 2016/0085302 | A1* | 3/2016 | Publicover | G06V 40/19 |
| | | | | 345/633 |
| 2017/0172675 | A1* | 6/2017 | Jarc | A61B 34/35 |
| 2018/0160035 | A1 | 6/2018 | Cleveland | |

(Continued)

FOREIGN PATENT DOCUMENTS

EP 3395251 10/2018

OTHER PUBLICATIONS

Joseph Redmon et al., IEEE, You Only Look Once: Unified, Real-Time Object Detection. (Year: 2016).*

(Continued)

*Primary Examiner* — Joshua B Blanchette
(74) *Attorney, Agent, or Firm* — Kilpatrick Townsend & Stockton LLP

(57) ABSTRACT

Systems and methods for eye tracking and content tagging in minimally invasive surgical videos are described herein. Minimally invasive surgical videos may be captured while performing robotic surgeries. Robotic surgical systems described herein include robotic arms with interchangeable surgical tools. An endoscope at the end of one of the robotic arms captures video of the surgical procedure. The video is displayed on a display of the surgical system and an eye tracking device captures data corresponding to a gaze direction of the user on the display. Content tags are automatically generated in the image data based on areas of focus of the user. Information within the content tag may be generated based on surgical procedure steps derived from the image data, a log of current surgical procedures, and image data of previous surgical procedures.

24 Claims, 7 Drawing Sheets

(56) References Cited

U.S. PATENT DOCUMENTS

2018/0239144 A1* 8/2018 Woods .................. A63F 13/213
2019/0008595 A1   1/2019 Popovic et al.
2019/0279765 A1* 9/2019 Giataganas ............. G06F 3/014

OTHER PUBLICATIONS

Eddie Forson, Medium.com, Understanding SSD MultiBox â Real-Time Object Detection In Deep Learning (Year: 2017).*
Cognolato M, Atzori M, Muller H. Head-mounted eye gaze tracking devices: An overview of modern devices and recent advances. J Rehabil Assist Technol Eng. Jun. 11, 2018;5:2055668318773991. doi: 10.1177/2055668318773991. PMID: 31191938; PMCID: PMC6453044.*

* cited by examiner

AUTOMATIC CONTENT TAGGING IN VIDEOS OF MINIMALLY INVASIVE SURGERIES

CROSS-REFERENCE TO RELATED APPLICATIONS

This application claims priority to U.S. Provisional Patent Application No. 62/935,899, filed Nov. 15, 2019, titled "Automatic Content Tagging in Videos of Minimally Invasive Surgeries," the entirety of which is hereby incorporated by reference.

BACKGROUND

In recent years, robotic surgeries have become increasingly popular because of their advantages over traditional human-operated surgeries. Surgical tools used in robotic surgeries enable a human surgeon to have improved levels of dexterity, range of motion, and precision. In most robotic surgical systems, these tools are connected to robotic arms and interchangeable depending on the surgery to be performed.

BRIEF SUMMARY

Various examples are described including systems, methods, and devices relating to eye tracking and content tagging in surgical videos during a surgical procedure.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method including receiving sensor data indicating a gaze location of a user with respect to a display device during a surgical procedure. The computer-implemented method also includes receiving image data of the surgical site during the surgical procedure from a camera. The computer-implemented method includes determining an area of interest within the image data based on the sensor data. The computer-implemented method also includes generating a content tag that identifies the area of interest within the image data and associating the content tag with the area of interest. The computer-implemented method also includes storing the image data with the content tag.

One general aspect includes a computer-implemented method including receiving sensor data indicating a gaze location of a surgeon on a display during a surgical procedure. The computer-implemented method also includes receiving image data of the surgical site during the surgical procedure from a camera corresponding to a view of the surgeon on the display during the surgical procedure. The computer-implemented method also includes determining an area of interest within the image data based on the sensor data and generating a content tag that identifies the area of interest within the image data. The computer-implemented method also includes determining a surgical procedure step based on the area of interest. The computer-implemented method also includes generating content for the content tag based on the surgical procedure step and associating the content tag with the area of interest. The computer-implemented method also includes storing the image data with the content tag. Other embodiments of this aspect include corresponding computer systems, apparatus, and computer programs recorded on one or more computer storage devices, each configured to perform the actions of the methods.

Another general aspect includes a computer-implemented method including receiving sensor data indicating a gaze location of a user during a surgical procedure and receiving image data of the surgical procedure from a camera. The computer-implemented method also includes determining, based on the sensor data, an area of interest within the image data identifying the gaze location of the user on a display device, the display device displaying the image data. The computer-implemented method includes detecting that the area of interest is offset from a center of the display device and generating, based on detecting that the area of interest is offset from the center of the display, a notification recommending adjusting a position or orientation of the camera. Other embodiments of this aspect include corresponding computer systems, apparatus, and computer programs recorded on one or more computer storage devices, each configured to perform the actions of the methods.

Another general aspect includes a computer-implemented method including receiving image data of a surgical procedure from a camera and presenting the image data on a display device. The computer-implemented method also includes receiving sensor data identifying a gaze location, or alternatively a gaze direction, of a surgeon during the surgical procedure. The computer-implemented method also includes identifying, based on the sensor data, an area of interest within the image data on the display device. The computer-implemented method includes accessing a database of surgical procedure image data based on the area of interest. The computer-implemented method also includes determining an expected gaze location of the surgeon based on the database of surgical procedure image data and determining that the gaze location of the surgeon differs from the expected gaze location. The computer-implemented method also includes generating a notification based on the gaze location of the surgeon differing from the expected gaze location. Other embodiments of this aspect include corresponding computer systems, apparatus, and computer programs recorded on one or more computer storage devices, each configured to perform the actions of the methods.

Another general aspect includes one or more non-transitory computer-readable media including computer-executable instructions that, when executed by one or more computing systems, cause the one or more computing systems to receive sensor data indicating a gaze location of a surgeon on a display during a surgical procedure and to receive image data of the surgical procedure from a camera. The instructions further cause the computing systems to determine an area of interest within the image data based on the sensor data. The instructions further cause the computing systems to generate a content tag that identifies the area of interest within the image data and associate the content tag with the area of interest. The instructions further cause the computing systems to store the image data with the content tag.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
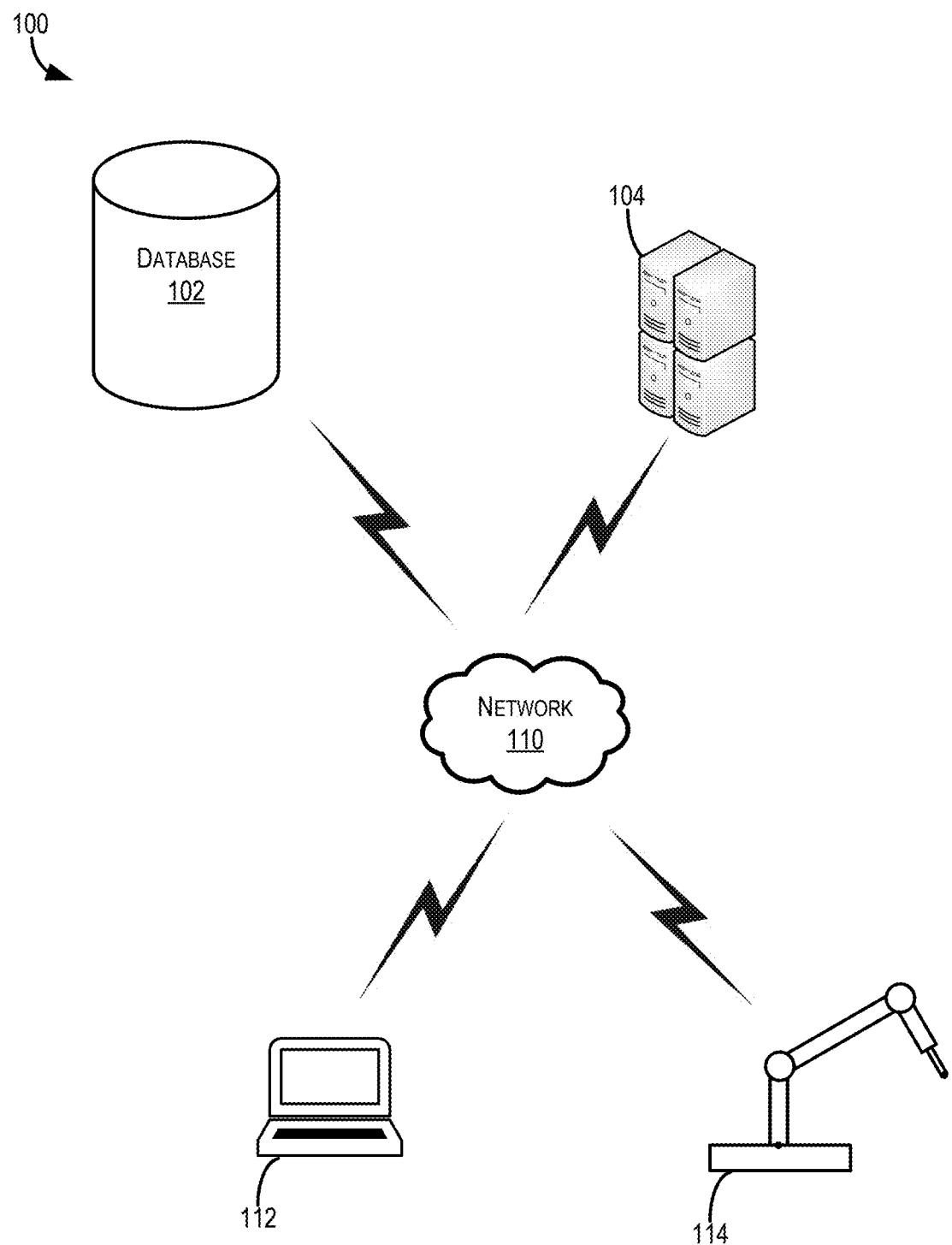
FIG. 1 illustrates a block diagram illustrating an example system for automatically tagging videos of minimally invasive surgeries, according to at least one example.

Examples are described herein in the context of eye tracking during minimally invasive surgeries for identifying and tagging areas of interest within image data of surgical videos. Those of ordinary skill in the art will realize that the following description is illustrative only and is not intended to be in any way limiting. For example, although the example methods for identifying and tagging areas of interest are described with reference to robotic surgical systems, these methods may be implemented in other systems that utilize video recording in connection with movements of robots or non-robotic minimally invasive surgeries. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a robotic surgical system includes one or more robotic arms, each having a surgical tool connected to it. A camera, e.g., an endoscope, is connected to one of the robotic arms to capture images or videos of a surgical procedure performed using the surgical tools. The robotic surgical system also includes a surgeon console having a display for managing operation of the robotic arms (e.g., enabling a surgeon to operate the surgical tools) and for viewing video from the camera. The system also includes an eye tracking system for determining a gaze direction and a gaze point of a user (e.g., the surgeon) on the display of the console. The robotic surgical system also includes a computer system having software loaded thereon to enable automatic tagging and content generation in surgical video data captured by the camera using the gaze direction of the user.

In this illustrative example, the eye tracking system determines a gaze point of the user on the display of the console throughout the surgical procedure. The computer system identifies areas of focus of the user with respect to time and based on the gaze point of the user, and uses the areas of focus to generate content tags. The computer system then associates the content tags with the image data captured by the camera at the corresponding times. These areas of focus may correspond to important areas of the patient anatomy, and may also correspond to distinct steps of the surgical procedure. In some examples, the gaze direction of the user may be used to identify the areas of interest, the gaze direction of the user being determined by a computing device in communication with a gaze direction detector system such as a head direction detection system that identifies a gaze direction of the user based on the head direction of the user.

The computer system described herein may perform additional processes using data from the eye tracking system and the image data gathered by the camera. For example, after generating the content tag described above, the computer system may compare the image data and data describing the areas of focus to previous surgical images containing content tags including procedure steps, instructions, or notes related to the surgical procedure being performed. The computer system may then identify similar procedure steps and generate notes, instructions, procedure information, and/or other information relating to the step to populate the content tag to describe the step being performed.

In addition to generating the content tags as described above, the computer system may track the gaze point of a user on the display of the surgical device and identify areas of focus, such as when a user's gaze point remains within a small area or a blink rate of the user slows. When this occurs, the computer system may instruct a robotic arm including the camera to adjust its location to center a view of the camera at the gaze point, i.e., center the view on the display. Alternatively or additionally, the computer system may generate a notification to the user recommending movement of the view of the camera to center on the gaze point of the user at the center of the display.

In some examples, the computer system may maintain content tags and data that associate a user area of focus, a step in a surgical procedure, and information related to what is depicted within the surgical image data. This data may be stored for later reference and comparison against current or future surgical procedures. For example, the computer system may identify the gaze point of the user or of another operator or observer during a surgical procedure using data from the eye tracking system. From this, the computer system may identify an area of focus within the image data of the surgical procedure. In a later surgical procedure, the computer system may gather similar data to that previously gathered and stored as described above and compare the gaze point of the user in the present surgical procedure, in relation to patient anatomy within the field of view of the camera, to previous surgical procedure image data. The computer system may identify when a user's area of focus is in a location other than an expected gaze point based on the previous surgical procedure image data. For example, the user may be looking at one site within the surgical region while it is expected they would be focused in a separate area based on the step being performed according to the previous surgical image data. The computer system may make a recommendation to adjust the gaze area of the user as described above, based on the gaze area not matching the expected gaze area. In some examples, the computer system also makes a recommendation of a gaze area for the user on the display to assist the user throughout a surgical procedure.

The systems and methods described in further detail below may increase the speed at which surgical videos can be annotated as compared to typical approaches. For example, in a typical surgical annotation system, a user watches a recording of a surgical video and manually inserts annotations into the surgical video. In the system and methods described herein, content tags are generated automatically by tracking the gaze area of the user during the surgical procedure and identifying areas of focus and generating content tags associated with the areas of focus. Additionally, the systems and methods herein further increase the speed of surgical video annotation by automatically generating content for the content tag to describe procedure steps, insert notes, or other content for the annotations within the video based on previously annotated surgical videos. These annotations may then be used to process aggregate data for surgeries of a particular type and provide area of focus guidance or hints in subsequent procedures.

Furthermore, the systems and methods described herein improve the gathering of surgical image data during a surgical procedure by assisting a user in maintaining the area of focus in the surgical procedure at the center of a display on a robotic surgical system. The systems and methods described herein may further provide training to users (e.g., to increase safety and efficiency of surgical procedures by ensuring that a focus area of the user matches an expected focus area). The user may be notified, for example, when their focus is in a different area of the surgical site than expected, or the system may provide a graphical overlay on surgical video to highlight an expected area of focus.

This illustrative example is given to introduce the reader to the general subject matter discussed herein and the disclosure is not limited to this example. The following sections describe various additional non-limiting examples and methods relating to eye tracking techniques for gaze correction and automatic tagging of surgical image data.

Turning now to the figures, FIG. 1 illustrates a block diagram of an example system 100 for automatically tagging videos of minimally invasive surgeries, according to at least one example. The system 100 includes computing device 104, surgical device 114, surgical console 112, and database 102. The surgical device 114 includes any suitable number of robotic arms, as described in additional detail with respect to FIG. 2. In some examples, the surgical device 114 may be a non-robotic surgical device and instead be any sort of minimally invasive surgery device. The computing device 104, the database 102, and the surgical console 112 may be in network communication with each other as shown through network 110. As described in additional detail with respect to FIGS. 4 and 5, the computing device 104 includes software components to perform the processes described herein. In some examples, the computing device 104 may be incorporated in or part of the surgical console 112. As described below with respect to FIG. 2, the surgical console 112 is a computing device from which a user may control the surgical device 114 and view imagery related to a surgical operation via a connected display, such as from an endoscope. The surgical console 112 also includes an eye tracking device (not shown in FIG. 1) for tracking the gaze of a user on the display.

The computing device 104, as described herein, is any suitable electronic device (e.g., personal computer, handheld device, server computer, server cluster, virtual computer, etc.) configured to execute computer-executable instructions to perform operations such as those described herein. The components of the system 100 are connected via one or more communication links with the network 110. The network 110 includes any suitable combination of wired, wireless, cellular, personal area, local area, enterprise, virtual, or other suitable network.

It should be understood that although FIG. 1 illustrates the various components, such as the database 102, the surgical console 112, and the computing device 104 as independent elements, they may be included in a single computing device 104 or in communication over the network 110. Additionally, the functionality described herein need not be separated into discrete elements, or some or all of such functionality may be located on a computing device remote from the surgical device 114, the surgical console 112, or the computing device 104 such as a central controlling device connected to the surgical device 114 directly or through the network 110 and configured to control the components of the system 100.

Figure 2:
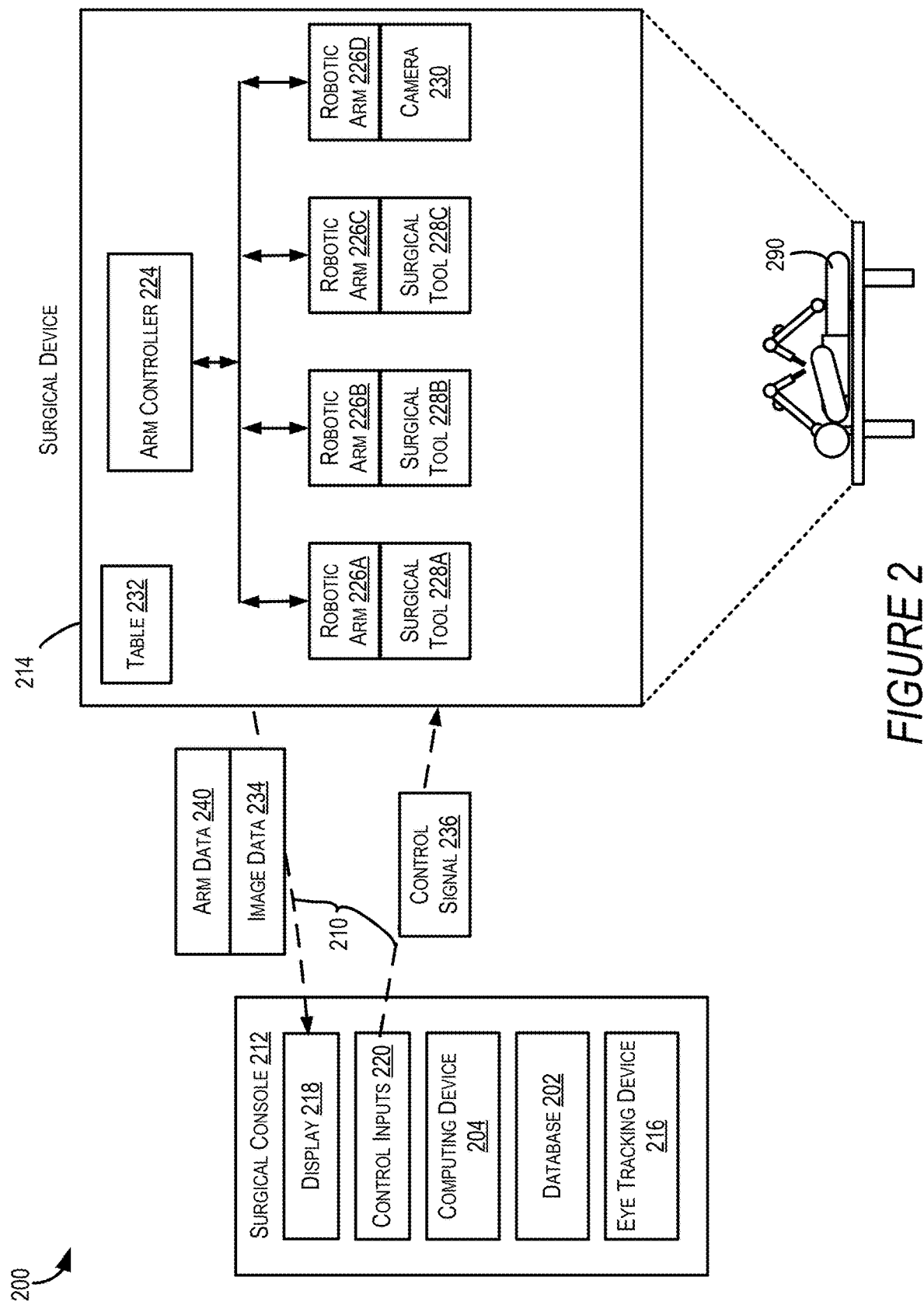
FIG. 2 illustrates an example system for automatically tagging videos of minimally invasive surgeries, according to at least one example.

FIG. 2 illustrates a system 200 for automatically tagging videos of minimally invasive surgeries, according to at least one example. In the system 200, the surgical device 214 is configured to operate on a patient 290. The system 200 also includes a surgical console 212 connected to the surgical device 214 and configured to be operated by a surgeon to control and monitor the surgeries performed by the surgical device 214. The system 200 might include additional stations (not shown in FIG. 2) that can be used by other personnel in the operating room, for example, to view surgical information, image data, etc., sent from the surgical device 214. The surgical device 214, the surgical console 212, and other stations can be connected directly or through the network 210, such as a local-area network ("LAN"), a wide-area network ("WAN"), the Internet, or any other networking topology known in the art that connects the surgical device 214, the surgical console 212 and other stations.

The surgical device 214 can be any suitable robotic system that can be used to perform surgical procedures on the patient 290. The surgical device 214 includes one or more robotic arms 226A-D (which may be referred to herein individually as a robotic arm 226 or collectively as the robotic arms 226) connected to a base such as a table 232. The robotic arms 226 may be manipulated by control inputs 220, which may include one or more user interface devices, such as joysticks, knobs, handles, or other rotatable or translatable devices to effect movement of one or more of the robotic arms 226. The robotic arms 226A-C may be equipped with one or more surgical tools 228A-C to perform aspects of a surgical procedure. For example, the robotic arms 226A-C may be equipped with surgical tools 228A-228C, (which may be referred to herein individually as a surgical tool 228 or collectively as the surgical tools 228). The surgical tools 228 can include, but are not limited to, tools for grasping for holding or retracting objects, such as forceps, graspers and retractors, tools for suturing and cutting, such as needle drivers, scalpels and scissors, and other tools that can be used during a surgery. Each of the surgical tools 228 can be controlled by the surgeon through the surgical console 212 including the control inputs 220.

Different surgical devices may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without robotic arms, such as for endoscopy procedures, may be employed according to different examples. It should be understood that while only one surgical device 214 is depicted, any suitable number of surgical devices 214 may be employed within system 200.

The surgical device 214 may also be any other minimally invasive surgical system which includes the use of a camera 230 and displays the view from the camera 230 on a display 218 for a surgeon to view. For example, endoscopic, endovascular, and laparoscopic surgeries may be performed with non-robotic surgical devices and include a camera 230 to view the surgical procedure site.

The surgical device 214 is also equipped with one or more cameras 230, such as an endoscope camera, configured to provide a view of the operating site to guide the surgeon during the surgery. In some examples, the camera 230 can be attached to one of the robotic arms 226D. In some examples, the camera 230 can be attached to a mechanical structure of the surgical device 214 that is controlled separately from the robotic arms 226 or is stationary with respect to the surgical device 214.

The surgical device 214 includes an arm controller 224. The arm controller 224 controls the positioning and movement of the robotic arms 226 based on a control signal 236 from the surgical console 212 generated by the control inputs 220.

The surgical console 212 includes a display 218 for providing a feed of image data 234 from the camera 230 as well as patient anatomy models and depth information gathered by the system 200. The image data 234 is transferred to the surgical console 212 over the network 210 along with arm data 240 describing the position of each of the robotic arms 226. The computing device 204 described in FIG. 2 is shown included in the surgical console 212 but may also be located remotely of the surgical console 212 as described above. Additionally, the database 202, which may include surgical procedure information and previous surgical image data is included in the surgical console 212. The computing device 204 presents the image data 234 received from camera 230 on the display 218.

The eye tracking device 216 tracks the gaze of the user on the display 218. The eye tracking device 216 may include a hardware device as well as software on the computing device 204 to track the gaze of the user. Any suitable eye tracking system known in the art may be used as the eye tracking device 216. Many typical eye tracking devices rely on reflections or glints on the eye of the user to track the gaze direction of the user. For example, some eye tracking devices include a hardware device that is mounted adjacent to a display and includes one or more emitters and one or more cameras. The emitters emit light, visible or infrared, and the one or more cameras capture images of the eyes including glints or reflections of the light from the emitters. The gaze direction of the user may be determined based on the location of the glints on the eye of the user as captured in the images. In some examples, the system 200 may include a head direction tracker for determining a gaze direction of the user based on the position of the head of the user rather than solely an eye tracking device. In some examples, the head direction tracker may be used to determine when the user is looking at the display 218 or to a general area of the display, such as a particular quadrant, while the eye tracking device 216 may then be used to track the gaze direction only when the head direction indicates the user is looking at the display 218 or to refine the gaze point of the user within the quadrant identified by the head direction tracker.

Figure 3:
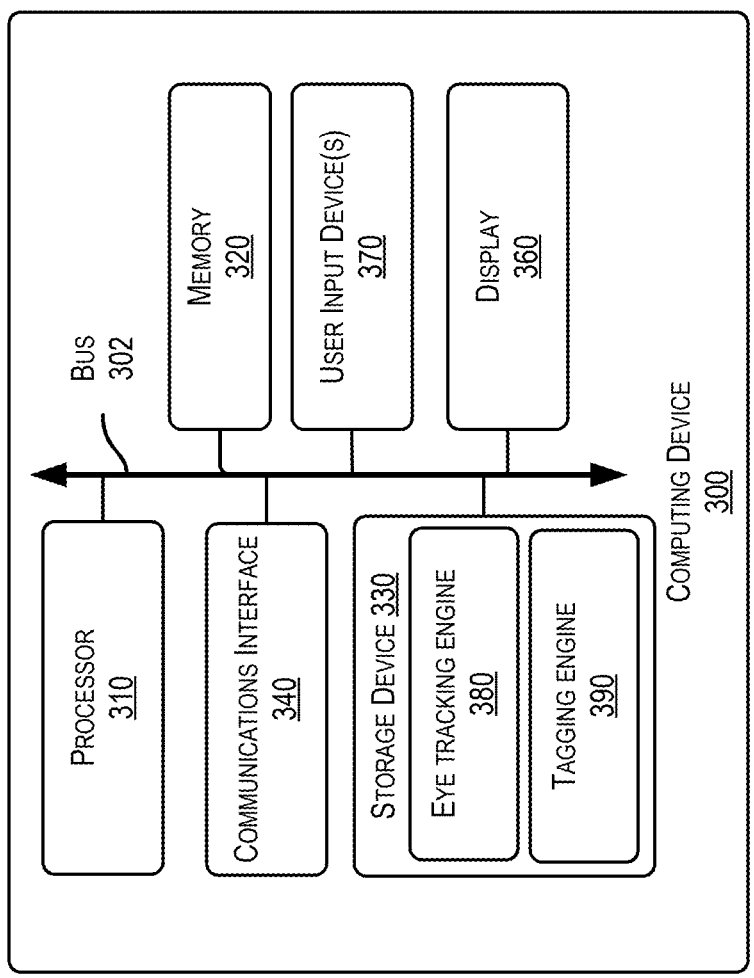
FIG. 3 illustrates a simplified block diagram depicting an example computing device for automatically tagging videos of minimally invasive surgeries, according to at least one example.

Referring now to FIG. 3, FIG. 3 shows a simplified block diagram depicting an example computing device 300 for automatically tagging videos of minimally invasive surgeries, according to at least one example. For example, computing device 300 may be the computing device 104 of FIGS. 1 and 2. Computing device 300 includes a processor 310 which is in communication with the memory 320 and other components of the computing device 300 using one or more communications buses 302. The processor 310 is configured to execute processor-executable instructions stored in the memory 320 to track the gaze direction of the surgeon and generate content tags according to different examples, such as part or all of the example processes 600, 700, 800, and 900 described below with respect to FIGS. 6, 7, 8 and 9. The computing device 300, in this example, also includes one or more user input devices 370, such as a keyboard, mouse, touchscreen, microphone, etc., to accept user input. The computing device 300 also includes a 360 display to provide visual output to a user.

The computing device 300 can include or be connected to one or more storage devices 330 that provides non-volatile storage for the computing device 300. The storage devices 330 can store system or application programs and data used by the computing device 300, such as an eye tracking engine 380 and a tagging engine 390. The storage devices 330 might also store other programs and data not specifically identified herein.

The computing device 300 also includes a communications interface 340. In some examples, the communications interface 340 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array ("FPGA") specifically to execute the various methods. For example, examples may be implemented in digital electronic circuitry, or in computer hardware, firmware, software, or in a combination thereof. In one example, a device may include a processor or processors. The processor has a computer-readable medium, such as a random access memory ("RAM") coupled to the processor. The processor executes computer-executable program instructions stored in memory, such as executing one or more computer programs. Such processors may include a microprocessor, a digital signal processor ("DSP"), an application-specific integrated circuit ("ASIC"), field programmable gate arrays ("FPGAs"), and state machines. Such processors may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

Such processors may include, or may be in communication with, media, for example computer-readable storage media, that may store instructions that, when executed by the processor, can cause the processor to perform the steps described herein as carried out, or assisted, by a processor.

Examples of computer-readable media may include, but are not limited to, an electronic, optical, magnetic, or other storage device capable of providing a processor, such as the processor in a web server, with computer-readable instructions. Other examples of media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may include code for carrying out one or more of the methods (or parts of methods) described herein.

Turning now to the eye tracking engine 380, generally, the eye tracking engine 380 determines a gaze direction or a gaze point of a user on a display device (e.g., the display 218) based on data received from the eye tracking device 216. The eye tracking engine 380 also determines an expected gaze point based on previous surgical procedure data from the database 202. The eye tracking engine 380 may include eye tracking software or algorithms for use with the eye tracking device 216 to perform gaze detection and gaze point determinations. Further details regarding the processes performed by the eye tracking engine 380 are described with reference to processes 400, 500, 600, and 700 below.

The eye tracking engine 380 interfaces with the eye tracking device 216 such as an eye tracking device or other such hardware and receives eye tracking data. In some instances, the eye tracking data may describe a head direction, gaze direction, or other data that is useable for determining a gaze point of a user. The eye tracking engine 380 alone, or in combination with the eye tracking device 216, gathers stores, and interprets the eye tracking data to determine a gaze point of the user on the display 218.

The eye tracking engine 380 determines the gaze direction or the gaze point of the user on the display 218 by using the eye tracking data and identifying an intersection of the gaze direction of the user with the display 218. This may include software or programs known to those with skill in the art for tracking gaze direction, head direction, or gaze points of the user. The eye tracking engine 380 may also determine an area of focus of the user by tracking gaze point over time, identifying an area of focus when the gaze point of user is stationary or contained within a certain area. In some examples, the focus area of the user may be determined based on blink frequency, with lower blink frequency associated with an area of focus of the user.

The eye tracking engine 380 may also cause the computing device 204 to determine when the area of focus of the user is at or near the center of the display 218. In instances when the area of focus is away from the center of the display 218, such as at the edge of the display 218, the computing device 204 may also generate a notification to the user instructing them to reposition the camera 230 to center the area of focus within the display 218.

The eye tracking engine 380 causes the computing device 204 to communicate with the database 202 to determine an expected gaze point of the user on the display 218. The computing device 204 determines the expected gaze point by analyzing previous surgical data from previous surgical procedures performed and tagged with an area of focus. The computing device 204 further compares the area of focus in the present surgical procedure with the area of focus in the previous surgical procedures based on content tags identifying the area of focus in the previous surgical procedure. The computing device 204 may also generate a notification to the user when the area of focus of the user does not match the expected area of focus of the user as determined by the computing device 204.

Generally, the tagging engine 390 generates content tags and places them within the surgical videos to identify areas of interest, areas of focus, or to include procedure notes, based on data received from the eye tracking device 216 or eye tracking engine 380. The tagging engine 390 causes the computing device 204 to interface with the database 202 to access content tag information, such as content to include in the surgical video data tags as well as information related to generating tags, such as requirements for amount of time a user is focused on a particular area before a tag is generated. Additionally, the tagging engine 390 causes the computing device 204 to access the previous image data of previous surgical procedures for comparison to present surgical image data, according to at least some of the methods described below with respect to FIGS. 4-7.

The tagging engine 390 causes the computing device 204 to generate content tags for surgical image data and the content tags identify locations in the surgical image data. Additionally, the content tags are associated with one or more frames of the image data 234 or with a timestamp of the surgical video. The content tags accompany the surgical image data as metadata indicating the areas of importance within the surgical image data with a time and a location within a frame of the surgical image data. The content tags mark areas of focus or importance within the surgical image data. In typical systems, the tags must be manually added with notes following the surgical procedure, which is a time consuming and slow process.

The location of the content tags may be based on the computing device 204 identifying gaze locations in the previous surgical procedure image data and identifying corresponding locations in the image data 234 of the present surgical procedure. In some examples, the content tag location may also be based on content tags within the previous surgical procedure image data. In some examples, the content tag location is determined by identifying similar anatomy or surgical sites in the present image data using object recognition techniques known to those with skill in the art. The object recognition technique may identify similar anatomy within the image data as compared to the previous image data and after identifying corresponding anatomy, identifying an expected gaze location based on the metadata or content tags of the previous image data.

The tagging engine 390 causes the computing device 204 to automatically generate the tags based on eye tracking data from the eye tracking system and in some examples also generates notes or populates the tag with comments or notes regarding the procedure step being performed or other surgical notations. A graphical element may also be generated by the tagging engine 390 to be embedded within the surgical image data. The graphical element may include an arrow, box, circle, or other indicator to draw attention to the area of importance identified by the content tags. In some examples, the graphical elements may be generated and stored separately from the surgical image data but added to and overlaid on the surgical image data when played back for review. Alternatively, the computing device that later displays the surgical image data may generate one or more graphical overlays based on the associated content tags.

The tagging engine 390 also causes the computing device 204 to display the image data as well as the content tags on the display 218. The tagging engine 390 further causes the computing device 204 and eye tracking device 216 to track the gaze point of the user on the display 218. In some examples, a graphical element, such as described above, may be generated on the display to indicate the location of the gaze point of the user for reference. This graphical element may also be included with the image data as it is stored, described below.

The tagging engine 390 causes the computing device 204 to store the image data as well as the associated content tags on the database 202 for later reference. The tagging engine 390 may embed the content tags in the image data or may associate the content tags with times and location in the image data, such as in a separate file from the surgical image data, as described above with respect to the content tags and graphical elements.

It should be understood that although FIG. 3 illustrates various components, such as the eye tracking engine 380, the tagging engine 390, and the database 202, that are included in the computing device 204 or in communication over the network 210, one or more of these elements may be implemented in different ways within the system 200. For example, the functionality described above need not be separated into discrete elements, or some or all of such functionality may be located on a computing device remote from the surgical device 214, the surgical console 212, or the computing device 204 such as a central controlling device connected to the surgical device 214 directly or through the network 210 and configured to control the components of the system 200.

FIGS. 4-7 illustrate example flow diagrams showing processes 400, 500, 600, and 700 according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

Figure 4:
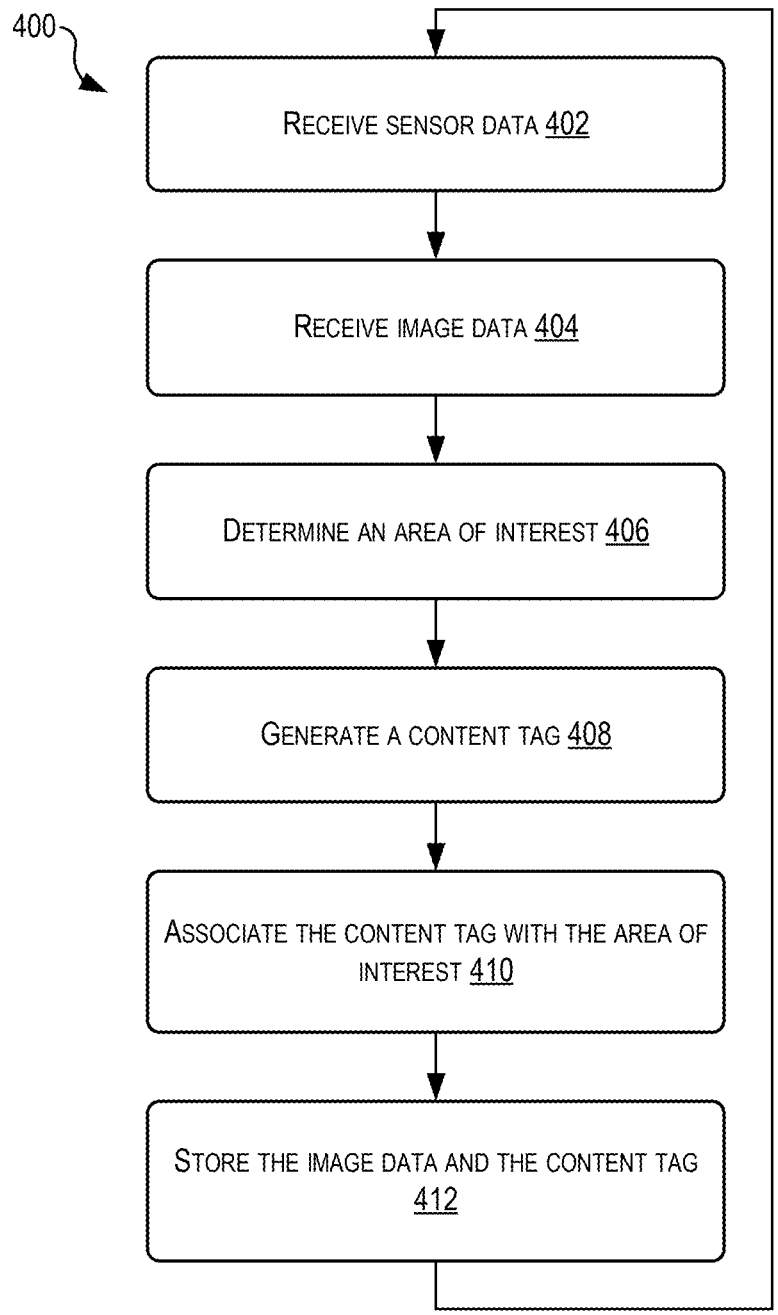
FIG. 4 illustrates an example flow chart depicting an example process for automatically tagging surgical videos, according to at least one example.

Turning now to FIG. 4, FIG. 4 illustrates an example flow chart depicting a process 400 for automatically tagging surgical videos, according to at least one example. The process 400 is performed by the computing device 204 (e.g., the eye tracking engine 380 and/or the tagging engine 390) though in some cases may be performed by other software elements of the computing device 204. The process 400 in particular corresponds to automatically tagging surgical image data during a minimally invasive surgical procedure.

The process 400 begins at block 402 by the computing device 204 receiving sensor data from the eye tracking device 216. The sensor data relates to the gaze direction of the user on the display 218 and may relate to a head direction of a user. The sensor data may include eye glint data. The eye glint data may be used to identify particular curvatures or positions of the eye based on common eye characteristics and calibration data or processes performed during setup of the eye tracking device 216. The eye glint data is gathered by capturing images of reflections from emitted lights of the eye tracking system 216. For example, the eye tracking system 216 may include a number of illuminators and a number of cameras, the illuminators causing reflections on the eye of the user when illuminated and the cameras capturing the reflections. The eye glint data, including the reflections, is then analyzed by software associated with the eye tracking system 216 to determine a gaze direction of the user. The sensor data may correspond to a gaze point of the user on the display 218. The sensor data may also include other data relating to the user, such as the size of the user's pupils, the blink frequency, or other indicators of focus by the eyes of the user. In some examples, the computing device 204 may also store user specific data, such as information related to a user's pupil size, interpupillary distance, or calibration data for the eye tracking system 216. This data can be accessed as part of a user profile selected by the user so it need not be re-acquired with each use of the eye tracking system 216.

In some examples, the eye tracking technique may rely on other forms of eye tracking and gaze direction tracking including optical techniques such as described above, eye-attached trackers such as contact lenses, or any other suitable gaze direction tracking device known in the art.

At block 404, the computing device 204 receives image data 234 from the camera 230. The image data 234 may include image data, images, or other representations of the view of the camera 230. The image data 234 represents the field of view captured by the camera 230 of the surgical procedure site. The image data 234 may also include data relating to how the image data is displayed on the display 218. For example, this may include a change in the aspect ratio, a cropped perimeter, or other adjustments to the image data 234 to make it fit the display 218.

Block 404 may also include the computing device 204 causing the image data 234 to be displayed on the display 218 of the surgical device 214. This may include conveying the image data 234 as it is relayed from the camera 230, providing an up-to-date view of the surgical site. The image data 234 may include up-to-date videos or still images captured by the camera 230.

At block 406, the computing device 204 determines an area of interest within one or more image frames represented by the image data 234. In some examples, the area of interest may be determined by identifying portions of the screen where the user gazes for an extended period of time based on the sensor data from the eye tracking device 216 and corresponds to a region or area of the image data 234 displayed on the display 218 where the user is focusing. For example, the computing device 204 may identify an area of interest based on a user's gaze area remaining within a limited region of the display 218 for longer than a predetermined threshold of time, such as a second or a few seconds. The computing device 204 may make this determination based on a number of factors, such as the gaze direction of the user remaining unchanged or within a predetermined confined area for a predetermined period of time, such as several seconds. In an example, the user's gaze direction may remain within a one inch by one inch area of the display for a predetermined period of time, indicating the user is focusing in that area. Additionally, the computing device 204 may determine the focus area based on other characteristics of the user and the user's eyes such as a blink frequency decreasing while focusing or a speed of eye movement decreasing. In some examples, other factors such as pupil size may also be used to identify when a user is focusing on a particular area of the display 218.

The area of interest may be determined based on a weighted average of the gaze locations of the user. For example, the user may be looking around the display 218 but primarily in and around one specific location. The computing device 204 may determine, based on a weighted average of the gaze locations over time, that the area of interest is at the specific location with the highest length of time the gaze location was in the vicinity.

In some examples, the area of interest may be determined based on a predictive model, such as described below with respect to the expected gaze location of FIG. 7. Based on previous surgical procedure image data, the computing device 204 may predict an expected area of interest by referencing previous areas of interest or content tags in previous image data.

At block 408, the computing device 204 generates a content tag. The content tag corresponds to the area of interest identified in block 406. The content tag may be stored separately as metadata associated with the image data 234 identifying a location and a time stamp in the image data 234 for the area of interest. In some examples, the computing device may also provide a visual marker or graphical element within the image data 234 identifying the area of interest. In some examples, the content tag may also include notes or information regarding the surgical procedure. In some examples, the content tags are associated with physical objects within the image data 234. For instance, the computing device 204 may identify or recognize, using object recognition techniques, what the user is gazing at. The user may be gazing at the appendix in an appendectomy that the computing device 204 recognizes and associates the content tag with the recognized anatomy. This allows comparison of the image data 234 to previous or future image data when the field of view differs but the computing device 204 is still able to identify the appendix in the previous or future image data. Such information may be generated by the computing device 204 as described below with respect to FIG. 5 or may be manually input by a user.

The location of the content tag may be based on the computing device 204 identifying gaze locations in the previous surgical procedure image data and identifying corresponding locations in the image data 234 of the present surgical procedure. In some examples, the content tag location may also be based on content tags within the previous surgical procedure image data. In some examples, the content tag location is determined by identifying similar anatomy or surgical sites in the present image data using object recognition techniques known to those with skill in the art, including those described above with respect to FIG. 5. The object recognition technique may identify similar anatomy within the image data as compared to the previous image data and after identifying corresponding anatomy, identifying an expected gaze location based on the metadata or content tags of the previous image data.

At block 410, the computing device 204 associates the content tag with the area of interest in the image data 234. Associating the content tag with the area of interest in the image data 234 may include marking a location and a time within the image data 234 where the content tag identifies the area of interest. The location may be a certain location of pixels on the display 218, the location of an object (e.g., an appendix or physical anatomy), or a coordinate within the image data 234. The time may include the specific selected frame or a timestamp of the image data 234. In some examples this may include generating a graphical element to display a representation of the content tag within the image data 234. In some examples, the content tag may be separate from the image data 234 but include information such as a timestamp and a location within the display 218 for the content tag to be located.

At block 412, the computing device 204 stores the image data 234 and the content tag in the database 202. Storing the image data 234 and the content tag may include writing the image data and content tag separately on a storage device of the database 202 or may include storing the image data 234 with the content tag embedded therein on the database 202.

Following block 412, the process 400 returns to block 402 to repeat the process 400 throughout the surgical procedure. In some examples the process may be performed on each frame, every second to every few seconds, or at some other sampling rate, such as twice per minute.

Figure 5:
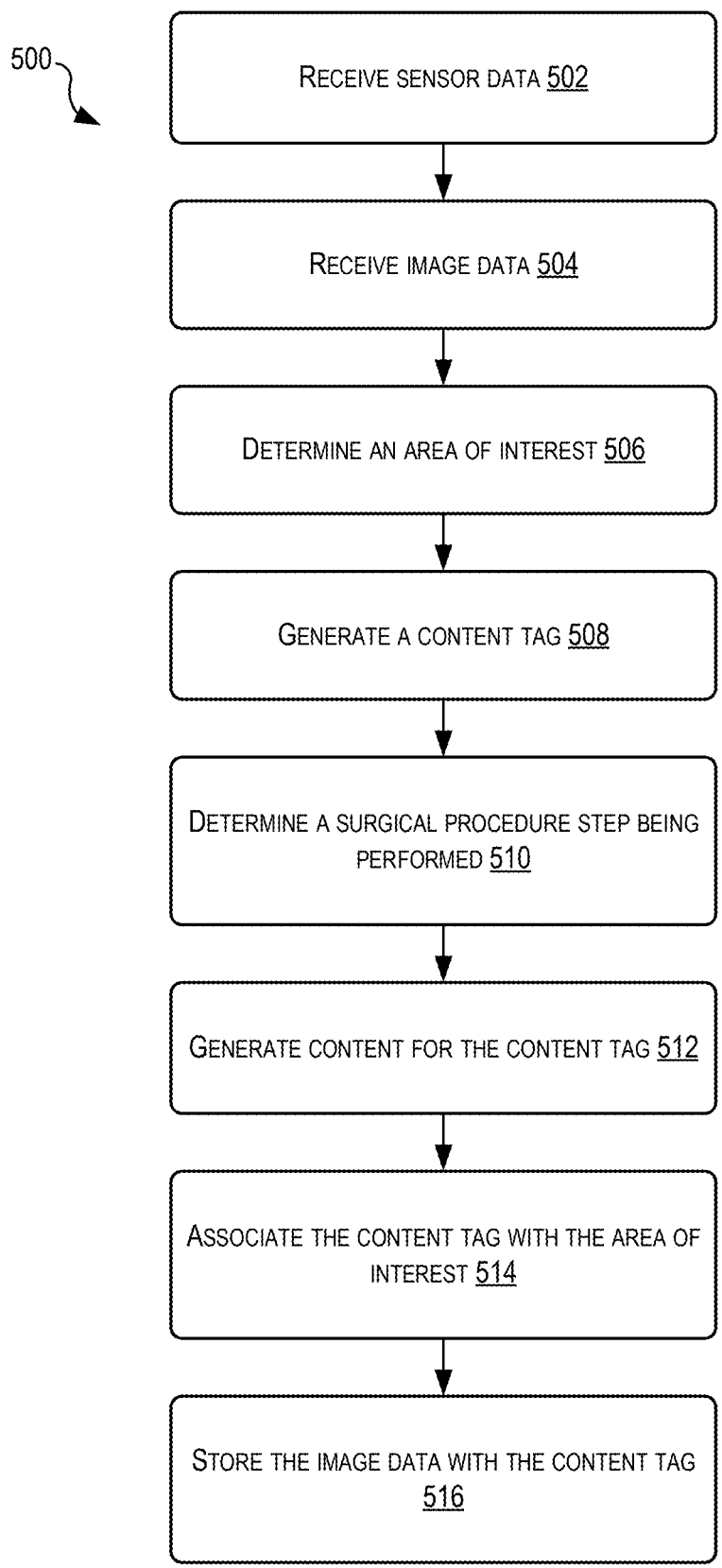
FIG. 5 illustrates an example flow chart depicting an example process for automatically tagging surgical videos, according to at least one example.

FIG. 5 illustrates an example flow chart depicting a process 500 for automatically tagging surgical videos, according to at least one example. The process 500 is performed by the computing device 204, such as the tagging engine 390. The process 500 includes generating content to populate or associate with the content tags rather than simply identifying the area of interest with a content tag.

The process 500 begins at block 502 with the computing device 204 receiving sensor data from the eye tracking device 216 as described with respect to block 402 above. The sensor data relates to the gaze direction of the user on the display 218 and may relate to a gaze direction as described above. The sensor data may include eye glint data for eye tracking systems and the sensor data may correspond to a gaze point on the display 218. The sensor data may also include other data relating to the use, such as the size of the user's pupils, the blink frequency, or other indicators of focus by the eyes of the user.

At block 504, the computing device 204 receives image data 234 from the camera 230 generally as described with respect to block 404 above. The image data 234 may include videos, images, or other representations of the view of the camera 230 in the minimally invasive procedure.

Block 504 may also include the computing device 204 causing the image data 234 to be displayed on the display 218 of the surgical device 214. This may include conveying the image data 234 as it is relayed from the camera 230, providing an up-to-date view of the surgical site. The image data 234 may include up-to-date videos or still images captured by the camera 230.

At block 506, the computing device 204 determines an area of interest within the image data 234 generally as described with respect to block 406 above. The area of interest is determined based on the sensor data from the eye tracking device 216 and corresponds to a region or area of the image data 234 displayed on the display 218 where the user is focusing. The computing device 204 may make this determination based on a number of factors, such as the gaze direction of the user remaining unchanged or within a predetermined confined area for a predetermined period of time, such as several seconds. In an example, the user's gaze direction may remain within a one inch by one inch area of the display for a predetermined period of time, indicating the user is focusing in that area. Additionally, the computing device 204 may determine the focus area based on other characteristics of the user and the user's eyes such as a blink frequency decreasing while focusing or a speed of eye movement decreasing. A decrease in the blink frequency of the user may indicate that they are focusing at that particular point in time, and the computing device 204 may identify the present gaze area when the user is appearing to focus and identify it as a focus area.

At block 508, the computing device 204 generates a content tag generally as described above with respect to block 408. The content tag corresponds to the area of interest identified in block 506. The content tag may provide a visual marker within the image data 234 identifying the area of interest. In some examples, the content tag may also include notes or information regarding the surgical procedure. Such information may be generated by the computing device 204 as described below with respect to FIG. 7 or may be manually input by a user.

At block 510, the computing device 204 determines a surgical procedure step being performed. In some examples, this step may involve a manual input by a user into the computing device 204. In some examples, the computing device 204 accesses previous surgical procedure data corresponding to previous surgical procedures and identifies surgical procedure steps based on content tags within the previous surgical procedure data. For example, the computing device 204 may identify twenty distinct steps performed as part of an appendectomy. Each step may describe independent or discrete movements during the surgical procedure. The computing device 204 further identifies, based on the image data 234, a surgical procedure step performed within the image data 234. This may, for example, rely on object recognition techniques known to those with skill in the art, such as approaches based on machine learning including scale-invariant feature transform which detects and described features in images. For instance, the computing device 204 may identify or recognize, using object recognition techniques, what the user is gazing at. The user may be gazing at the appendix in an appendectomy that the computing device 204 recognizes and may determine a procedure step based on the focus on the appendix. Other object-recognition techniques may include You Only Look Once (YOLO) or Single Shot Multibox Detector techniques or others known in the art.

The computing device 204 may identify the surgical procedure step being performed in the image data 234 by performing image analysis such as object recognition techniques known to those with skill in the art and comparing the positioning and movements of the surgical tools 228 against previous surgical procedure data containing content tags identifying particular procedure steps. In some examples, the surgical procedure step may be determined based on a previous surgical procedure step identified. For example, the computing device 204 may identify a first procedure step, such as the initial step of the surgical procedure, and based on information from previous surgical procedures may identify a subsequent surgical procedure step and thereby identify the procedure step being performed based on this previous step.

At block 512, the computing device 204 generates content for the content tag, such as associating the content from block 710 with the content tag. The content for the content tag includes the surgical procedure step identified at block 510. In some examples, the computing device automatically populates the content tag with this information. The tagging engine 390 may also generate content based on selecting content from a database of predetermined content selections. For example, an appendectomy may include standard or In some examples, the computing device may also include additional notes, such as regarding any abnormality or differences in the surgical procedure over previous surgeries based on comparison of the previous surgical images to the image data 234. The content may be added to by the user as well by manual addition.

At block 514, the computing device 204 associates the content tag with the area of interest in the image data 234 generally as described above with respect to block 410. Associating the content tag with the area of interest in the image data 234 may include marking a location and a time within the image data 234 where the content tag identifies the area of interest. In some examples this may include generating a graphical element to display a representation of the content tag within the image data 234. In some examples, the content tag may be separate from the image data 234 but include information such as a timestamp and a location within the display 218 for the content tag to be located.

At block 516, the computing device 204 stores the image data 234 and the content tag in the database 202 generally as described above with respect to block 412. Storing the image data 234 and the content tag may include writing the image data and content tag separately on a storage device of the database 202 or may include storing the image data 234 with the content tag embedded therein on the database 202. The content tag, including the content generated at block 512, is stored on the database 202 to preserve the content and make it available for later reference.

Figure 6:
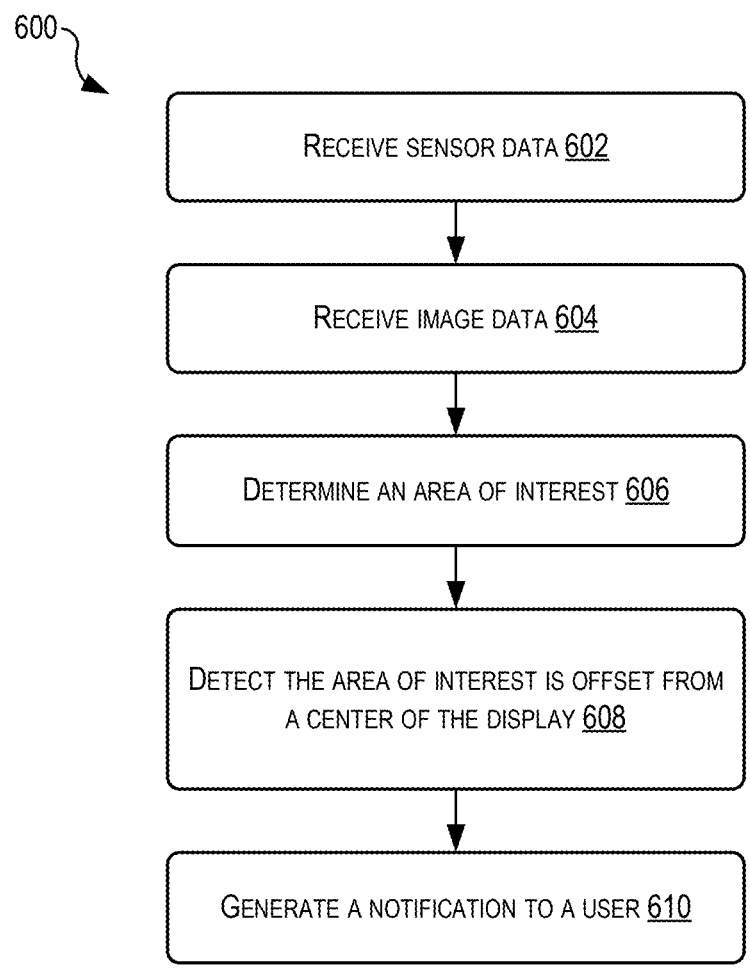
FIG. 6 illustrates an example flow chart depicting an example process for centering an area of interest in surgical videos on a display, according to at least one example.

FIG. 6 illustrates an example flow chart depicting a process 600 for centering an area of interest in surgical videos on the display 218, according to at least one example. The process 600 is performed by the computing device 204, and may specifically be performed by the eye tagging engine 380.

The process 600 begins at block 602 with the computing device 204 receiving sensor data from the eye tracking device 216 generally as described with respect to block 402 above. The sensor data relates to the gaze direction of the user on the display 218 and may relate to a head direction of a user. The sensor data may include eye glint data for eye tracking systems and the sensor data may correspond to a gaze point on the display 218. The sensor data may also include other data relating to the use, such as the size of the user's pupils, the blink frequency, or other indicators of focus by the eyes of the user.

At block 604, the computing device 204 receives image data 234 from the camera 230 generally as described with respect to block 404 above. The image data 234 may include videos, images, or other representations of the view of the camera 230 in the minimally invasive procedure. Block 404 may also include the computing device 204 causing the image data 234 to be displayed on the display 218 of the surgical device 214. This may include conveying the image data 234 as it is relayed from the camera 230, providing an up-to-date view of the surgical site. The image data 234 may include up-to-date videos or still images captured by the camera 230.

At block 606, the computing device 204 determines an area of interest within the image data 234 generally as described above with respect to block 406. The area of interest is determined based on the sensor data from the eye tracking device 216 and corresponds to a region or area of the image data 234 displayed on the display 218 where the user is focusing. The computing device 204 may make this determination based on a number of factors, such as the gaze direction of the user remaining unchanged or within a predetermined confined area for a predetermined period of time, such as several seconds. In an example, the user's gaze direction may remain within a one inch by one inch area of the display for a predetermined period of time, indicating the user is focusing in that area. Additionally, the computing device 204 may determine the focus area based on other characteristics of the user and the user's eyes such as a blink frequency decreasing while focusing or a speed of eye movement decreasing.

At block 608, the computing device 204 determines that the area of interest determined at block 606 is offset from a center of the display 218. The computing device 204 compares the location of the area of interest on the display 218 and determines whether the area of interest is at the center of the display 218. The center of the display may be the absolute center of the display 218, or may be a region of the display 218 at or near the center of the display 218. In some examples, the center of the display may encompass an area of the display 218 excluding only a perimeter of the display, such as within a few inches of the edges of the display 218. The center of the display 218 may be a small portion of the display 218 such as an area several inches square at the center of the display. The center of the display 218 may also be a larger area, including any portion of the display excluding a perimeter at the edge of the display 218 one to several inches wide.

At block 610, the computing device 204 generates a notification to the user that the area of interest is offset from the center of the display 218. The notification may be an audible notification, such as a beep or an audible voice notifying the user. In some examples, the notification may be tactile such as haptic feedback or may be a visual notification on the display 218. The notification may instruct the user to adjust the robotic arm to change the field of view of the camera 230 such that the area of interest is moved to a center of the field of view, which corresponds to the center of the display 218.

In some examples, the process 600 may further include adjusting the position of the camera 230 automatically based on the area of interest not being positioned at the center of the display. For example, following block 608, the computing device 204 may determine a set of adjustments to the position of the camera 230 to center the area of interest on the display 218. The computing device 204 may, for example, adjust the position of the camera 230 towards the right to move the area of interest from the left side of the display 218 to the center of the display 218.

Figure 7:
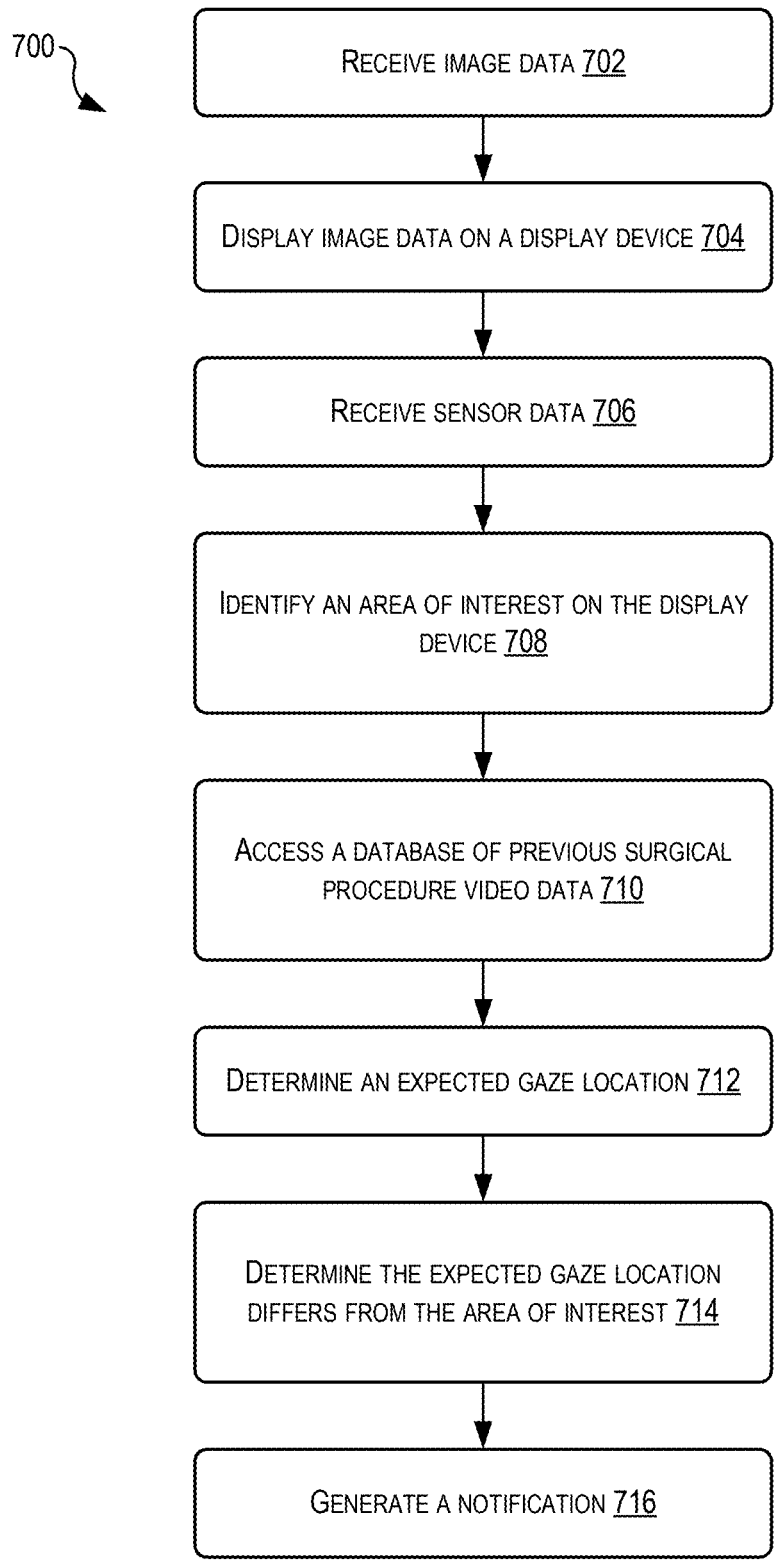
FIG. 7 illustrates an example flow chart depicting an example process for predicting an expected gaze point and notifying a user when their area of focus differs from the expected gaze point, according to at least one example.

FIG. 7 illustrates an example flow chart depicting a process 700 for predicting an expected gaze point and notifying a user when their area of focus differs from the expected gaze point, according to at least one example. The process 700 is performed by the computing device 204, or by software thereon, such as the eye tracking engine 380.

At block 702, the computing device 204 receives image data 234 from the camera 230, generally as described with respect to block 604 above. The image data 234 may include videos, images, or other representations of the view of the camera 230 in the minimally invasive procedure. The view of the camera 230 represents a field of view of a surgical procedure site.

At block 704, the computing device 204 causes the image data 234 to be displayed on the display 218 of the surgical device 214. This may include conveying the image data 234 as it is relayed from the camera 230, providing an up-to-date view of the surgical site. The image data 234 may include up-to-date videos or still images captured by the camera 230.

At block 706, the computing device 204 receives sensor data from the eye tracking device 216, generally as described with respect to block 602 above. The sensor data relates to the gaze direction of the user on the display 218 and may relate to a gaze direction or a head direction of a user. The sensor data may include eye glint data for eye tracking systems and the sensor data may correspond to a gaze point on the display 218. The sensor data may also include other data relating to the use, such as the size of the user's pupils, the blink frequency, or other indicators of focus by the eyes of the user.

At block 708, the computing device 204 determines an area of interest on the display 218, generally as described above with respect to block 606. The area of interest is determined based on the sensor data from the eye tracking device 216 and corresponds to a region or area of the image data 234 displayed on the display 218 where the user is focusing. The computing device 204 may make this determination based on a number of factors, such as the gaze direction of the user remaining unchanged or within a predetermined confined area for a predetermined period of time, such as several seconds. In an example, the user's gaze direction may remain within a one inch by one inch area of the display for a predetermined period of time, indicating the user is focusing in that area. Additionally, the computing device 204 may determine the focus area based on other characteristics of the user and the user's eyes such as a blink frequency decreasing while focusing or a speed of eye movement decreasing.

At block 710, the computing device 204 accesses previous surgical procedure image data from the database 202. The previous surgical procedure image data is of a surgical procedure similar to the surgical procedure being performed and includes content tags or other data corresponding to a focus area or gaze point of the user during the previous surgical procedure.

At block 712, the computing device 204 determines an expected gaze location of the user in the present surgical procedure within the image data 234 based on the previous surgical procedure image data from block 710. The expected gaze location is determined by analyzing previous image data of previous surgical procedures including metadata or tags that identify the gaze area of the surgeon or an area of interest in the previous image data. The expected gaze location may be based on the computing device 204 identifying gaze locations in the previous surgical procedure image data and identifying corresponding locations in the image data 234 of the present surgical procedure. In some examples, the expected gaze location may also be based on content tags within the previous surgical procedure image data. In some examples, the expected gaze location is determined by identifying similar anatomy or surgical sites in the present image data using object recognition techniques known to those with skill in the art, including those described above with respect to FIG. 5. The object recognition technique may identify similar anatomy within the image data as compared to the previous image data and after identifying corresponding anatomy, identifying an expected gaze location based on the metadata or content tags of the previous image data.

At block 714, the computing device 204 determines that the expected gaze location determined at block 712 differs from the area of interest identified in block 708. The computing device 204 makes this determination by comparing the expected gaze location to the area of interest. In some examples, the difference between the expected gaze location and the area of interest will exceed a predetermined threshold before the computing device 204 determines a meaningful difference exists. The comparison may be based on the expected gaze location being within a predetermined range, such as within one to several inches on the display 218.

At block 716, the computing device 204 generates a notification to the user notifying the user that the expected gaze location differs from the area of interest. The notification may be an audible notification, such as a beep or an audible voice notifying the user. In some examples, the notification may be tactile such as haptic feedback or may be a visual notification on the display 218, such as an arrow or a bounding box or circle around the expected area of interest. In some examples the notification may instruct the user of the expected gaze location and prompt them to adjust their area of focus accordingly.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. A computer-implemented method for automatically tagging videos of minimally invasive surgeries executed by a computing device, comprising:

receiving sensor data, including eye glint data, indicating a gaze location associated with a gaze of a user with respect to a display device during a surgical procedure performed using a robotic surgical system, the gaze associated with a gaze duration and the eye glint data based on information about one or more reflections from an eye of the user generated in response to light emitted by one or more illuminators;

receiving image data during the surgical procedure from a camera, wherein the camera is connected to a robotic arm of the robotic surgical system;

determining that the gaze location corresponds to an area of interest within the image data based on the sensor data, comprising:

determining, by the computing device, a portion of the display device corresponding to the gaze location of the user; and determining that the gaze duration exceeds a predetermined period of time;
generating a content tag that identifies the area of interest, wherein the content tag comprises: an anatomical location, a timestamp, and a note related to a surgical procedure step being performed, wherein the anatomical location is determined automatically using an objection recognition technique based on a scale-invariant feature transform, a you only look once (YOLO) technique, or a single shot multibox detector;
associating the content tag with the area of interest; and
storing information about the content tag as metadata for the image data, the metadata usable to generate one or more graphical overlays for the image data.

2. The computer-implemented method of claim 1, wherein determining the area of interest is further based on an eye movement speed.

3. The computer-implemented method of claim 1, wherein determining the area of interest is further based on an eye blink rate.

4. The computer-implemented method of claim 1, further comprising generating content for the content tag based on the image data describing processes performed during the surgical procedure.

5. The computer-implemented method of claim 4, wherein generating the content for the content tag comprises determining, based on the image data, the surgical procedure step being performed.

6. The computer-implemented method of claim 1, wherein determining the area of interest within the image data comprises identifying the anatomical location and the timestamp within the image data including the area of interest.

7. The computer-implemented method of claim 1, further comprising:
receiving surgical procedure type data associated with the surgical procedure;
comparing the content tag to a database of previous surgical procedures including previous content tags based on the surgical procedure type data; and
generating content for the content tag based on the previous content tags describing additional processes performed during the surgical procedure.

8. A computer-implemented method for automatically tagging videos of minimally invasive surgeries executed by a computing device, comprising:
receiving sensor data, including eye glint data, indicating a gaze location associated with a gaze of a surgeon on a display during a surgical procedure performed using a robotic surgical system, the gaze associated with a gaze duration and the eye glint data based on information about one or more reflections from an eye of the surgeon generated in response to light emitted by one or more illuminators;
receiving image data of the surgical procedure from a camera corresponding to a view of the surgeon on the display during the surgical procedure, wherein the camera is connected to a robotic arm of the robotic surgical system;
determining that the gaze location corresponds to an area of interest within the image data based on the sensor data, comprising:
determining, by the computing device, a portion of the display corresponding to the gaze location of the surgeon; and
determining that the gaze duration exceeds a predetermined period of time;
generating a content tag that identifies the area of interest within the image data, wherein the content tag comprises: an anatomical location and a timestamp, wherein the anatomical location is determined automatically using an objection recognition technique based on a scale-invariant feature transform, a you only look once (YOLO) technique, or a single shot multibox detector;
determining a surgical procedure step based on the area of interest;
generating content for the content tag based on the surgical procedure step associating the content tag with the area of interest; and
storing information about the content tag as metadata for the image data, the metadata usable to generate one or more graphical overlays for the image data.

9. The computer-implemented method of claim 8, wherein determining the area of interest is further based on a pupil size.

10. The computer-implemented method of claim 8, further comprising comparing the image data to a database of previous image data comprising previous content tags, and wherein the content for the content tag is further based on the database of previous image data.

11. The computer-implemented method of claim 8, wherein determining the area of interest is further based on a predictive model.

12. The computer-implemented method of claim 8, wherein determining the surgical procedure step is further based on a predictive model.

13. One or more non-transitory computer-readable media comprising computer-executable instructions that, when executed by one or more computing systems, cause the one or more computing systems to:
receiving sensor data, including eye glint data, indicating a gaze location associated with a gaze of a surgeon on a display during a surgical procedure performed using a robotic surgical system, the gaze associated with a gaze duration and the eye glint data based on information about one or more reflections from an eye of the surgeon generated in response to light emitted by one or more illuminators;
receive image data of the surgical procedure from a camera, wherein the camera is connected to a robotic arm of the robotic surgical system;
determine that the gaze location corresponds to an area of interest within the image data based on the sensor data, comprising:
determining, by the one or more computing systems, a portion of the display corresponding to the gaze location of the surgeon; and
determining that the gaze duration exceeds a predetermined period of time;
generate a content tag that identifies the area of interest within the image data, wherein the content tag comprises: an anatomical location, a timestamp, and a note related to a surgical procedure step being performed, wherein the anatomical location is determined automatically using an objection recognition technique based on a scale-invariant feature transform, a you only look once (YOLO) technique, or a single shot multibox detector;
associate the content tag with the area of interest; and
storing information about the content tag as metadata for the image data, the metadata usable to generate one or more graphical overlays for the image data.

14. The one or more non-transitory computer-readable media of claim 13, wherein generating for the content tag comprises:
   accessing a database of previous surgical procedures; and
   identifying, using a predictive model, the surgical procedure step.

15. The one or more non-transitory computer-readable media of claim 13, wherein determining that the gaze location corresponds to the area of interest further comprises:
   generating weight-averaged data of gaze locations based on the gaze location and time data; and
   selecting the area of interest based on the weight-averaged data.

16. The computer-implemented method of claim 1, wherein determining that the gaze location corresponds to the area of interest further comprises:
   generating weight-averaged data of gaze locations based on the gaze location and time data; and
   selecting the area of interest based on the weight-averaged data.

17. The computer-implemented method of claim 8, wherein determining that the gaze location corresponds to the area of interest further comprises:
   generating weight-averaged data of gaze locations based on the gaze location and time data; and
   selecting the area of interest based on the weight-averaged data.

18. The computer-implemented method of claim 1, wherein associating the content tag with the area of interest comprises marking the anatomical location and the timestamp within the image data, wherein the anatomical location is a location of pixels on the display device, a location of an object shown on the display device, or a coordinate within the image data.

19. The computer-implemented method of claim 1, wherein the camera is an endoscope camera that is controlled separately from the robotic arm.

20. The computer-implemented method of claim 1, wherein the sensor data further includes a pupil size for the user or a blink frequency for the user.

21. The computer-implemented method of claim 1, wherein determining the area of interest is further based on a predictive model.

22. The computer-implemented method of claim 21, wherein the area of interest is determined using the predictive model by referencing previous areas of interest or content tags in previous image data.

23. The computer-implemented method of claim 1, further comprising generating a graphical element to display a representation of the content tag within the image data.

24. The computer-implemented method of claim 8, further comprising generating a graphical element to display a representation of the content tag within the image data.

* * * * *